(12) United States Patent
Miyazawa et al.

(10) Patent No.: US 6,414,167 B1
(45) Date of Patent: Jul. 2, 2002

(54) OCTAFLUOROTRICYCLODECANE DERIVATIVES AND PROCESSES FOR PRODUCING SAME

(75) Inventors: Satoru Miyazawa; Michitaka Ootani; Kentaro Tsutsumi, all of Saitama (JP)

(73) Assignee: Central Glass Company, Limited, Ube (JP)

(*) Notice: Subject to any disclaimer, the term of this patent is extended or adjusted under 35 U.S.C. 154(b) by 0 days.

(21) Appl. No.: 09/883,349

(22) Filed: Jun. 19, 2001

(30) Foreign Application Priority Data

Jun. 19, 2000 (JP) ........................................ 2000-183510

(51) Int. Cl.[7] .................... C07D 303/00; C07C 49/813; C07C 47/28; C07C 43/02; C07C 35/22
(52) U.S. Cl. ...................... 549/512; 568/326; 568/445; 568/665; 568/817
(58) Field of Search ......................... 549/512; 568/326, 568/817, 665, 445

(56) References Cited

U.S. PATENT DOCUMENTS

| 5,015,761 A | * | 5/1991 | Lenselink et al. | 568/817 |
| 5,705,169 A | * | 1/1998 | Stein et al. | 568/326 |
| 6,271,193 B1 | * | 8/2001 | Sprecker et al. | 568/445 |

* cited by examiner

Primary Examiner—Alan L. Rotman
Assistant Examiner—Raymond Covington
(74) Attorney, Agent, or Firm—Crowell & Moring LLP

(57) ABSTRACT

The invention relates to a novel octafluorotricyclodecane derivative represented by the general formula (1),

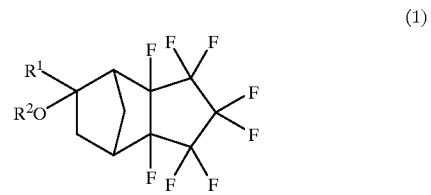

(1)

where $R^1$ is a hydrogen atom, a halogen atom, a hydrocarbon group or a halogenated hydrocarbon group, m is 0 or 1, and $R^2$ is represented by the general formula (2),

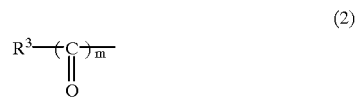

(2)

where $R^3$ is a hydrogen atom or a hydrocarbon group optionally having a substituent. This octafluorotricyclodecane derivative may be useful as a monomer for producing various functional polymers or as a raw material of the same.

21 Claims, No Drawings

OCTAFLUOROTRICYCLODECANE DERIVATIVES AND PROCESSES FOR PRODUCING SAME

BACKGROUND OF THE INVENTION

The present invention relates to novel fluorine-containing cycloalkane derivatives, which are useful as monomers for producing various functional polymers (having functions of water-repellency, oil-repellency, low water absorption, heat resistance, weatherability, corrosion resistance, transparency, photosensitivity and the like) and useful as raw materials of the same, and processes for producing such derivatives.

Aliphatic cyclic compounds, obtained by bonding a hydroxyl group to a ring (e.g., adamantane and bicycloalkane), have been used as monomers for producing functional polymers or as raw materials of the same. There is, however, a recent demand for novel monomers or their raw materials for providing superior functional polymers.

SUMMARY OF THE INVENTION

It is therefore an object of the present invention to provide a novel fluorine-containing cycloalkane derivative (e.g., an octafluorotricyclodecane derivative), which may be useful as a monomer for producing various functional polymers (having functions of water-repellency, oil-repellency, low water absorption, heat resistance, weatherability, corrosion resistance, transparency, photosensitivity and the like) or as a raw material of the same.

It is another object of the present invention to provide a process for producing such novel fluorine-containing cycloalkane derivative.

According to the present invention, there is provided an octafluorotricyclodecane derivative represented by the general formula (1),

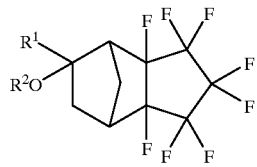
(1)

where $R^1$ is a hydrogen atom, a halogen atom, a hydrocarbon group or a halogenated hydrocarbon group, m is 0 or 1, and $R^2$ is represented by the general formula (2),

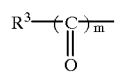
(2)

where $R^3$ is a hydrogen atom or a hydrocarbon group optionally having a substituent.

According to the present invention, there is provided a first process for producing a first octafluorotricyclodecane derivative represented by the general formula (6),

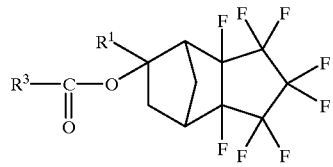
(6)

where $R^3$ is defined as above. The first process comprises reacting a second octafluorotricyclodecane derivative, which is represented by the general formula (4), with a carboxylic acid represented by the general formula (5),

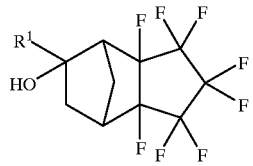
(4)

where $R^1$ is defined as above, $$R^3COOH \quad (5)$$

where $R^3$ is defined as above.

According to the present invention, there is provided a second process for producing an octafluorotricyclodecane derivative represented by the formula (8).

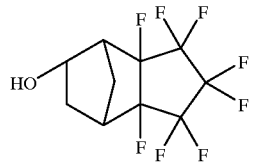
(8)

The second process comprises (a) conducting an epoxidation of 2,3,3,4,4,5,5,6-octafluorotricyclo[5.2.1.0$^{2,6}$]-8-decene, thereby obtaining an epoxy compound represented by the formula (7); and (b) reducing said epoxy compound into said octafluorotricyclodecane derivative.

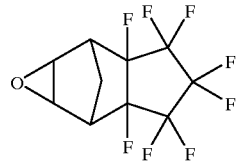
(7)

According to the present invention, there is provided a third process for producing an octafluorotricyclodecane derivative represented by the general formula (4). The third process comprises (a) conducting a rearragement reaction of an epoxy compound represented by the formula (7), thereby obtaining a ketone represented by the formula (9); (b) reacting said ketone with an organic metal compound represented by the general formula $R^1MX$ where $R^1$ is a hydrogen atom, a hydrocarbon group or a halogenated hydrocarbon group, M is a metal, and X is a halogen atom, thereby obtaining a product; and (c) hydrolyzing said product into said octafluorotricyclodecane.

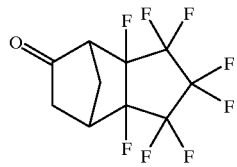

(9)

DESCRIPTION OF THE PREFERRED EMBODIMENTS

It is possible to efficiently produce the respective target octafluorotricyclodecane derivatives by the first to third processes.

As stated above, $R^1$ in the general formula (1) is a hydrogen atom, a halogen atom, a hydrocarbon group or a halogenated hydrocarbon group. This halogen atom may be fluorine, chlorine or bromine. Examples of the hydrocarbon group are $C_1$–$C_{20}$ hydrocarbon groups, such as methyl group, ethyl group, propyl group, isopropyl group, butyl group, isobutyl group, sec-butyl group, tert-butyl group, cyclopentyl group, cyclohexyl group, phenyl group, benzyl group, and phenethyl group. Of these, $C_1$–$C_{10}$ hydrocarbon groups are preferable, more preferably $C_1$–$C_4$ hydrocarbon groups. Examples of the halogenated hydrocarbon group are those obtained by partially or fully replacing hydrogen atoms of the above alkyl groups with halogen atoms, such as trifluoromethyl group, 2,2,2-trifluoroethyl group, 1,1,1,3,3,3-hexafluoroisopropyl group.

As stated above, $R^3$ in the general formula (2) is a hydrogen atom or a hydrocarbon group optionally having a substituent. This hydrocarbon group is preferably selected from $C_1$–$C_{20}$ hydrocarbon groups. Examples of the hydrocarbon group, which is free of a polymerizable double bond, are methyl group, ethyl group, propyl group, isopropyl group, butyl group, isobutyl group, sec-butyl group, tert-butyl group, cyclopentyl group, cyclohexyl group, phenyl group, benzyl group, and phenethyl group. Examples of the optional substituent are acyl group, allyl group, alkoxyl group, alkoxycarbonyl group, carboxyl group, carbonyl group, hydroxyl group, and nitrile group. Furthermore, $R^3$ may be a monovalent group represented by the general formula (3) having a polymerizable double bond,

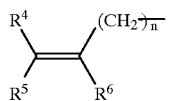

(3)

where each of $R^4$, $R^5$, and $R^6$ is independently a hydrogen atom, a halogen atom, or a hydrocarbon group optionally having a substituent, and n is an integer of 0–8. This halogen atom may be fluorine, chlorine or bromine. This hydrocarbon group is preferably selected from $C_1$–$C_{20}$ hydrocarbon groups, such as methyl group, ethyl group, propyl group, isopropyl group, butyl group, isobutyl group, sec-butyl group, tert-butyl group, cyclopentyl group, cyclohexyl group, phenyl group, benzyl group, and phenethyl group. Of these, $C_1$–$C_{10}$ hydrocarbon groups are preferable, more preferably $C_1$–$C_4$ hydrocarbon groups. Examples of the optional substituent are acyl group, allyl group, alkoxyl group, alkoxycarbonyl group, carboxyl group, carbonyl group, hydroxyl group, vinyl group, and nitrile group.

Concrete examples of $R^2$ are vinyl group, allyl group, acryloyl group and methacryloyl group.

The process for producing the octafluorotricyclodecane derivative represented by the general formula (1) will be described in detail in the following.

It is possible to produce the target octafluorotricyclodecane derivative represented by the general formula (1) from a starting material of 2,3,3,4,4,5,5,6-octafluorotricyclo[5.2.1.0$^{2,6}$]-8-decene by using the first, second or third process via an intermediate such as an epoxy derivative represented by the formula (7), a ketone derivative represented by the formula (9), and an alcohol derivative represented by the formula (4) or (8). In other words, each starting material, represented by the formula (4) or (7), of the first and third processes can be produced from 2,3,3,4,4,5,5,6-octafluorotricyclo[5.2.1.0$^{2,6}$]-8-decene In the invention, the process for synthesizing the octafluorotricyclodecane derivative (an epoxy compound) represented by the formula (7) is not particularly limited. For example, it can be synthesized by treating 2,3,3,4,4,5,5,6-octafluorotricyclo[5.2.1.0$^{2,6}$]-8-decene with a peracid in a solvent to proceed an epoxidation, as in the second process. This solvent is not particularly limited, so long as it can dissolve 2,3,3,4,4,5,5,6-octafluorotricyclo[5.2.1.0$^{2,6}$]-8-decene and the peracid. Exemplary solvents are methylene chloride, diethyl ether, and tetrahydrofuran. Examples of the peracid are peracetic acid, metachloroperbenzoic acid and monoperoxyphthalic acid. The temperature and the period of time for conducting the epoxidation may be suitably selected depending on the reagent types and the like. It is preferably conducted at a temperature of 0–100° C. for 1–48 hr.

In the invention, the process for synthesizing the octafluorotricyclodecane derivative (a ketone compound) represented by the formula (9) is not particularly limited. For example, it can be synthesized by a rearrangement reaction of the epoxy compound represented by the formula (7) using an acid catalyst, as in the third process. Examples of this acid catalyst are a complex of boron trifluoride and diethyl ether, Lewis acids (e.g., magnesium bromide), and mineral acids. It is possible to use a solvent in the rearrangement reaction. This solvent is not particularly limited, so long as it is inert in the reaction. Its examples are diethyl ether and benzene. The temperature and the period of time for conducting the rearrangement reaction may be suitably selected depending on the reagent types and the like. It is preferably conducted at a temperature of 0–100° C. for 1–48 hr.

In the invention, the process for synthesizing the octafluorotricyclodecane derivative (an alcohol compound) represented by the formula (8) is not particularly limited. For example, it can be synthesized through a hydration of 2,3,3,4,4,5,5,6-octafluorotricyclo[5.2.1.0$^{2,6}$]-8-decene with an acid aqueous solution. As another example, it can be synthesized by reducing the epoxy compound represented by the general formula (7), as in the second process. This reduction can be conducted by hydrogenating this epoxy compound with a metal hydride (e.g., lithium aluminum hydride, boron hydride, sodium hydride, and lithium hydride).

As shown in the third process, it is possible to synthesize the tertiary alcohol compound represented by the general formula (4), where $R^1$ is not a hydrogen atom nor a halogen atom, by reacting the ketone compound represented by the formula (9) with an organic metal compound in an organic solvent, followed by hydrolysis with water. This organic metal compound may be a Grignard's reagent or an organic lithium compound. This Grignard's reagent is represented by the general formula $R^1MX$ where $R^1$ is defined above, but is not a halogen atom; M is a metal (preferably magnesium); and X is a halogen (preferably chlorine, bromine or iodine). An example of this Grignard's reagent is an alkylmagnesium halide. The organic solvent is not particularly limited as long as it is inert in the reaction. Its examples are diethyl ether, tetrahydrofuran and hexane. Concrete examples of the organic metal compound are ethylmagnesium bromide and butyl lithium. The amount of the organic metal compound used in the reaction may be one to two equivalents per equivalent of the ketone compound. The temperature and the period of time for conducting the reaction of the ketone compound may be suitably selected depending on the organic metal compound type and the like. It is preferably conducted at a temperature of from −50 to 100° C. for about 3–48 hr.

As shown in the first process, it is possible to produce the octafluorotricyclodecane derivative (an ester compound) represented by the general formula (6) by reacting the octafluorotricyclodecane derivative (an alcohol compound) represented by the general formula (4) with a carboxylic acid represented by the general formula (5), $R^3COOH$. For example, it is possible to react this alcohol compound with this carboxylic acid (e.g., acrylic or methacrylic acid) in the presence of an acid catalyst (e.g., sulfuric acid) at a temperature of 20–120° C., thereby producing the target product (e.g., an acrylic or methacrylic ester).

In addition to the first to third processes, it is possible to react the octafluorotricyclodecane derivative (an alcohol compound) represented by the general formula (4) with a halide represented by the general formula (10), thereby producing the octafluorotricyclodecane derivative (a vinyl ether compound) represented by the general formula (11), $$R^3-X \tag{10}$$

where $R^3$ is defined as in the general formula (1), but is not a hydrogen atom, and X is chlorine, bromine or iodine.

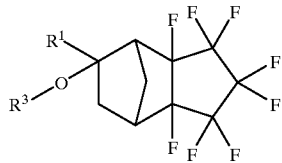

(11)

where $R^3$ is defined as in the general formula (1). For example, the reaction can be conducted in a solvent in the presence of a base at a temperature of 0–100° C. for about 3–48 hr. This solvent is not particularly limited so long as it is inert in the reaction. Its examples are ethers (e.g., tetrahydrofuran and diethyl ether), hydrocarbons (e.g., toluene and xylene), and dimethylformamide. The base can be selected from organic and inorganic bases such as triethylamine and sodium hydride. Alternatively, the vinyl ether compound can also be synthesized by reacting the alcohol compound represented by the general formula (4) with acetylene in the presence of a catalyst (e.g., an alkali metal oxide) at a temperature of 100–200° C. Furthermore, the target octafluorotricyclodecane derivative (an allyl ether) can be synthesized by reacting the alcohol compound represented by the general formula (4) with an allyl chloride at a temperature of 100–200° C.

Each target product obtained by the above-mentioned processes may be subjected to a conventional purification (e.g., concentration, distillation, extraction, recrystallization, filtration and column chromatography). It is possible to combine at least two of these.

The following nonlimitative examples are illustrative of the present invention.

EXAMPLE 1

Synthesis of 2,3,3,4,4,5,5,6-octafluorotricyclo[5.2.1.0$^{2,6}$]-8-decene

Under nitrogen gas flow, a 2-liter stainless steel (SUS) reaction tube was charged at room temperature with 747 g (3.52 mol) of octafluorocyclopentene and 74.0 g (1.12 mol) of cyclopentadiene. Then, the reaction tube was closed, followed by heating until 170° C. and then maintaining this temperature for 72 hr. Then, the reaction tube was cooled with ice, followed by decreasing the inside pressure. After that, the contents of the reaction tube were put into a 2-liter round-bottom flask, followed by vacuum distillation. With this, 193 g (0.694 mol, yield: 62.0% (standard: cyclopentadiene)) of a distillate of 52–55° C./12 mmHg were collected. The identification of the obtained compounds were conducted by nuclear magnetic resonance analysis ($^1H$, $^{13}C$, $^{19}F$) and infrared spectroscopic analysis. The results of these analyses are as follows. The obtained products 1 and 2 are isomers.

$^1$H-NMR(CDCl$_3$, TMS standard)

Product 1:

δ: 6.13(2H, br-s) 3.24(2H, br-s) 2.45(1H, dd, J=10.0 Hz, 1.2 Hz) 2.18(1H, dd, J=10.2 Hz, 1.2 Hz)

Product 2:

δ: 6.48(2H, br-s) 3.39(2H, d, J=1.2 Hz) 1.87-1.78(1H, m) 1.74(1H, br-d, J=11.6 Hz)

IR(neat)

ν (cm$^{-1}$): 1333, 1291, 1180, 1168

The sequential steps (a), (b) and (c) were conducted, as follows.

(a) Synthesis of Epoxy Compound Represented by the Formula (7)

Under an atmosphere of nitrogen gas, a 25-ml round-bottom flask was charged at room temperature with 261.5 mg (0.9402 mmol) of 2,3,3,4,4,5,5,6-octafluorotricyclo [5.2.1.0$^{2,6}$]-8-decene and 3.1 ml of dichloromethane. Then, 695.3 mg (2.8205 mmol) of metachloroperbenzoic acid were added at room temperature, followed by stirring at room temperature for 48 hr. Then, a sodium hydrogen sulfite aqueous solution (8.4615 mmol) was added in a dropwise manner at room temperature, thereby decomposing an excess of the reagent. After that, the reaction mixture was diluted with a large amount of ethyl acetate, followed by washing with 0.5 N sodium hydroxide aqueous solution, saturated sodium hydrogencarbonate aqueous solution, ion-exchanged water, and saturated brine. The resulting organic layer was dried with magnesium sulfate and then concentrated under vacuum with an evaporator. The obtained mixture was purified by silica gel chromatography (ethyl acetate/n-hexane=0/1–1/5), thereby obtaining 138.5 mg (0.4709 mmol) of the epoxy compound.

(b) Synthesis of Alcohol Compound Represented by the Formula (8)

Under an atmosphere of nitrogen gas, a 25 ml round-bottom flask was charged with 102.4 mg (0.3481 mmol) of the epoxy compound obtained in the step (a). Then, 13.2 mg (0.3481 mmol) of lithium aluminum hydride were added under cooling with ice bath, followed by stirring at 0° C. for 3 hr and then at room temperature for 12 hr. Then, the reaction mixture was diluted with a large amount of tetrahydrofuran. After that, 20 μl of ion-exchange water were added, followed by stirring at room temperature for 1 hr, thereby decomposing an excess of the reagent. The resulting precipitate was separated by filtration using silica gel, followed by concentration under vacuum with an evaporator. The obtained mixture was purified by silica gel chromatography (ethyl acetate/n-hexane=1/8–1/2), thereby obtaining 68.7 mg (0.2319 mmol) of the alcohol compound.

(c) Synthesis of Methacrylic Ester Represented by the Following Formula (12)

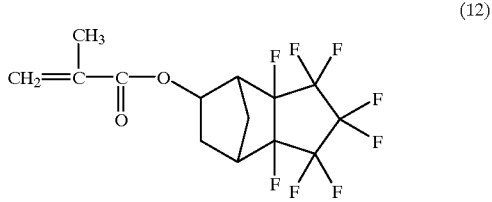

(12)

Under an atmosphere of nitrogen gas, a 25-ml round-bottom flask was charged at room temperature with 68.7 mg (0.2319 mmol) of the alcohol compound obtained in the step (b), 0.3 ml (3.4796 mmol) of methacrylic acid, and 2.5 mg (0.0232 mmol) of hydroquinone. Then, 35.9 mg (0.3479 mmol) of concentrated sulfuric acid were added at room temperature, followed by stirring at 60° C. for 5 hr. Then, the reaction mixture was cooled down until room temperature, followed by dilution with a large amount of ethyl acetate. After that, ion-exchanged water was added. The resulting organic layer was washed with a saturated sodium hydrogencarbonate aqueous solution, ion-exchanged water and saturated brine.

The obtained organic layer was dried with magnesium sulfate and then concentrated under vacuum with an evaporator.

The obtained mixture was purified by silica gel column chromatography (ethyl acetate/n-hexane=1/10), thereby obtaining 54.1 mg (0.1485 mmol) of the methacrylic ester. The identification of the obtained compound was conducted by nuclear magnetic resonance analysis ($^1$H, $^{19}$F) and infrared spectroscopic analysis. The results of these analyses are as follows.

$^1$H-NMR(CDCl$_3$, TMS standard)

δ: 6.07-6.00(1H, m), 5.54(1H, t, J=1.2 Hz), 5.19(1H, d, J=7.2 Hz), 2.97(1H, s), 2.84(1H, d, J=4.4 Hz), 2.55(1H, dd, J=14.8 Hz, 7.2 Hz), 2.15-2.11(1H, m), 1.96-1.68(4H, m), 1.59-1.53(1H, m) IR(neat)

ν (cm$^{-1}$): 2960, 1730, 1450, 1320, 1160, 1040, 950, 810

EXAMPLE 2

Synthesis of Ketone Represented by the Formula (9)

Under an atmosphere of nitrogen gas, a 25 ml round-bottom flask was charged at room temperature with 145.5 mg (0.4947 mmol) of an epoxide represented by the formula (7) and 4.9 ml (0.1 M) of benzene. The identification of this epoxide was conducted by nuclear magnetic resonance analysis. The results of this analysis are as follows.

$^1$H-NMR(CDCl$_3$, TMS)

major product

δ: 3.58(2H, s), 3.17(2H, s), 1.66(1H, ddd, J=12.4, 7.6, 7.6 Hz), 1.14(1H, d, J=12.4 Hz)

minor product

δ: 3.34(2H, s), 3.19-3.11(2H, m), 1.96(1H, d, J=11.6 Hz), 1.83(1H, d, J=11.6 Hz)

Then, 43.8 μl (0.4947 mmol) of trifluoromethanesulfonic acid were added, followed by heating for 24 hr under reflux condition. Then, ion-exchanged water was added to the reaction liquid under cooling with ice, followed by dilution with a large excess of ethyl acetate. The resulting organic layer was washed with 0.5 N sodium hydroxide aqueous solution and saturated brine. The obtained organic layer was dried with magnesium sulfate and then concentrated under vacuum with an evaporator. The obtained mixture was purified by silica gel chromatography (ethyl acetate/n-hexane=1/7), thereby obtaining 94.1 mg (0.3201 mmol) of the ketone. The identification of the obtained compound was conducted by nuclear magnetic resonance analysis ($^1$H, $^{19}$F), infrared spectroscopic analysis and mass spectrometry analysis. The results of NMR analysis are as follows.

$^1$H-NMR(CDCl$_3$, TMS)

major product

δ: 3.31-3.26(1H, m), 3.26(1H, s), 2.68(1H, dd, J=18.4, 4.4 Hz), 2.42(1H, ddd, J=18.4, 5.2, 4.8), 2.13(1H, d, J=12. Hz), 2.07-1.96(1H, m)

Synthesis of Tertiary Alcohol Represented by the Formula (4)

Under an atmosphere of nitrogen gas, a 25 ml round-bottom flask was charged at room temperature with 53.1 mg (0.1805 mmol) of the above-obtained ketone and 1.8 ml (0.1 M) of tetrahydrofuran. Then, the reaction solution was cooled down to −78° C., and 270.8 μl of a tetrahydrofuran solution containing 0.2708 mmol of ethylmagnesium bromide were added. After that, the temperature of the reaction mixture was gradually raised up to −20° C. Then, the flask was allowed to stand for 24 hr at −20° C. After that, a saturated ammonium chloride aqueous solution was added under cooling with ice bath, thereby decomposing an excess of the reagent. Then, the reaction mixture was diluted with a large excess of ethyl acetate. The resulting organic layer was washed with a saturated ammonium chloride aqueous solution and saturated brine. The obtained organic layer was dried with magnesium sulfate and then concentrated under vacuum with an evaporator. The obtained mixture was purified by silica gel chromatography (ethyl acetate/n-hexane=1/10), thereby obtaining 35.7 mg (0.1101 mmol) of the tertiary alcohol. The identification of the obtained compound was conducted by nuclear magnetic resonance analysis ($^1$H, $^{19}$F), infrared spectroscopic analysis and mass spectrometry analysis. The results of NMR analysis are as follows.

$^1$H-NMR(CDCl$_3$, TMS)

major product

δ: 2.83(1H, br-s), 2.69(1H, br-s), 2.40(1H, d, J=16.4 Hz), 2.02-1.93(1H, m), 1.96(1H, br-s), 1.83(1H, ddd, J=13.2, 8.4, 8.4 Hz), 1.72(1H, dq, J=13.2, 7.2 Hz), 1.68(1H, dq, J=13.2, 7.2Hz) 1.62(1H, br-d, J=13.2 Hz), 1.01(3H, t, J=7.2 Hz)

The entire disclosure of Japanese Patent Application No. 2000-183510 filed on Jun. 19, 2000, including specification, claims and summary, of which priority is claimed in the present application, is incorporated herein by reference in its entirety.

What is claimed is:

1. An octafluorotricyclodecane derivative represented by the general formula (1),

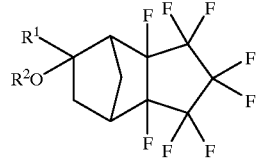
(1)

where $R^1$ is a hydrogen atom, a halogen atom, a hydrocarbon group or a halogenated hydrocarbon group, m is 0 or 1, and $R^2$ is represented by the general formula (2),

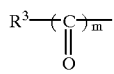
(2)

where $R^3$ is a hydrogen atom or a hydrocarbon group optionally having a substituent.

2. An octafluorotricyclodecane derivative according to claim 1, wherein said $R^3$ is a monovalent group represented by the general formula (3),

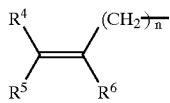
(3)

where each of $R^4$, $R^5$, and $R^6$ is independently a hydrogen atom, a halogen atom, or a hydrocarbon group optionally having a substituent, and n is an integer of 0–8.

3. An octafluorotricyclodecane derivative according to claim 1, wherein said $R^2$ is a vinyl group, an allyl group, an acryloyl group, or a methacryloyl group.

4. An octafluorotricyclodecane derivative according to claim 1, wherein said $R^1$ has a carbon atom number of 1–20.

5. An octafluorotricyclodecane derivative according to claim 1, wherein said $R^1$ has a carbon atom number of 1–10.

6. An octafluorotricyclodecane derivative according to claim 1, wherein said $R^1$ has a carbon atom number of 1–4.

7. An octafluorotricyclodecane derivative according to claim 1, wherein said $R^3$ has a carbon atom number of 1–20.

8. An octafluorotricyclodecane derivative according to claim 1, wherein said $R^3$ has a carbon atom number of 1–10.

9. An octafluorotricyclodecane derivative according to claim 1, wherein said $R^3$ has a carbon atom number of 1–4.

10. A process for producing a first octafluorotricyclodecane derivative represented by the general formula (6), said process comprising reacting a second octafluorotricyclodecane derivative, which is represented by the general formula (4), with a carboxylic acid represented by the general formula (5),

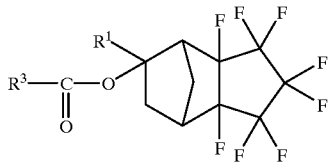
(6)

where $R^3$ is a hydrogen atom or a hydrocarbon group optionally having a substituent,

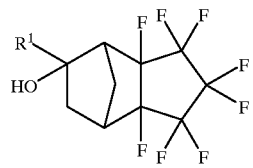
(4)

where $R^1$ is a hydrogen atom, a halogen atom, a hydrocarbon group or a halogenated hydrocarbon group,

$R^3COOH$ (5)

where $R^3$ is defined as above.

11. A process according to claim 10, wherein said carboxylic acid is methacrylic acid or acrylic acid.

12. A process according to claim 10, wherein said reacting is conducted in the presence of an acid catalyst.

13. A process for producing an octafluorotricyclodecane derivative represented by the formula (8), said process comprising:

(a) conducting an epoxidation of 2,3,3,4,4,5,5,6-octafluorotricyclo[5.2.1.0$^{2,6}$]-8-decene, thereby obtaining an epoxy compound represented by the formula (7); and (b) reducing said epoxy compound into said octafluorotricyclodecane derivative,

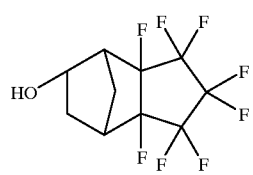
(8)

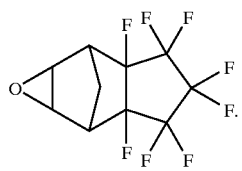
(7)

14. A process according to claim 13, wherein said epoxidation is conducted by treating said 2,3,3,4,4,5,5,6-octafluorotricyclo[5.2.1.0$^{2,6}$]-8-decene with a peracid in a solvent.

15. A process according to claim 13, wherein said reducing is conducted by hydrogenating said epoxy compound with a metal hydride.

16. A process for producing an octafluorotricyclodecane derivative represented by the general formula (4), said process comprising:

(a) conducting a rearragement reaction of an epoxy compound represented by the formula (7), thereby obtaining a ketone represented by the formula (9);

(b) reacting said ketone with an organic metal compound represented by the general formula $R^1MX$ where $R^1$ is a hydrogen atom, a hydrocarbon group or a halogenated hydrocarbon group, M is a metal, and X is a halogen atom, thereby obtaining a product; and (c) hydrolyzing said product into said octafluorotricyclodecane.

17. A process according to claim 16, wherein said rearrangement reaction is conducted in the presence of an acid catalyst.

18. A process according to claim 16, wherein said organic metal compound is an alkylmagnesium halide.

19. A compound represented by the formula (7),

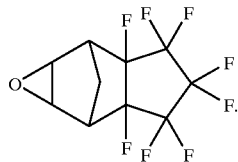

(7)

20. A compound represented by the formula (8),

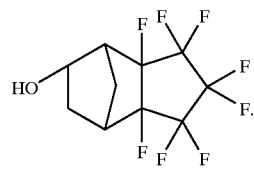

(8)

21. A compound represented by the formula (9),

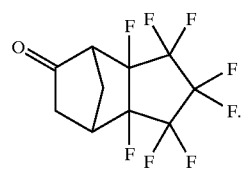

(9)

* * * * *